United States Patent
Kuo

(10) Patent No.: US 6,434,773 B1
(45) Date of Patent: Aug. 20, 2002

(54) DENTIFRICE DISPENSING ELECTRICAL TOOTHBRUSH WITH SNAP-ON DUAL BRUSH UNIT

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 0 days.

(21) Appl. No.: 09/649,074

(22) Filed: Aug. 28, 2000

(51) Int. Cl.[7] ............................................. A46B 13/04
(52) U.S. Cl. .............................. 15/22.1; 15/28; 15/29
(58) Field of Search ............................. 15/22.1, 28, 29

(56) References Cited

U.S. PATENT DOCUMENTS

| | | | | |
|---|---|---|---|---|
| 3,195,537 A | * | 7/1965 | Blasi | |
| 5,301,381 A | * | 4/1994 | Klupt | |
| 5,461,744 A | * | 10/1995 | Merbach | |
| 5,476,384 A | * | 12/1995 | Giuliani et al. | |
| 5,504,959 A | * | 4/1996 | Yukawa et al. | |
| 5,524,312 A | * | 6/1996 | Tan et al. | |
| 5,909,977 A | * | 6/1999 | Kuo | |

* cited by examiner

*Primary Examiner*—Terrence R. Till
(74) *Attorney, Agent, or Firm*—Fred L. Denson

(57) ABSTRACT

A dentifrice dispensing electrical toothbrush having two replaceable oscillating brush elements. A motor, batteries and a cartridge that contains dentifrice material are housed in the toothbrush handle. A neck connects the brush head and the handle. A pair of brush elements is mounted on a pair of posts attached to the brush head in a manner that allows their free oscillation. The neck includes a flow channel for dentifrice material that is pumped from the cartridge to the spout opening at the base of one of the brush elements. The brush elements are detachably positioned on the brush head by a snap-on retention cradle and are replaceable by detachment of the retention cradle from the brush head. An oscillating motion is imparted to both brush elements by an oscillating means and a drive shaft that is positioned in the neck and connected to the motor.

27 Claims, 17 Drawing Sheets

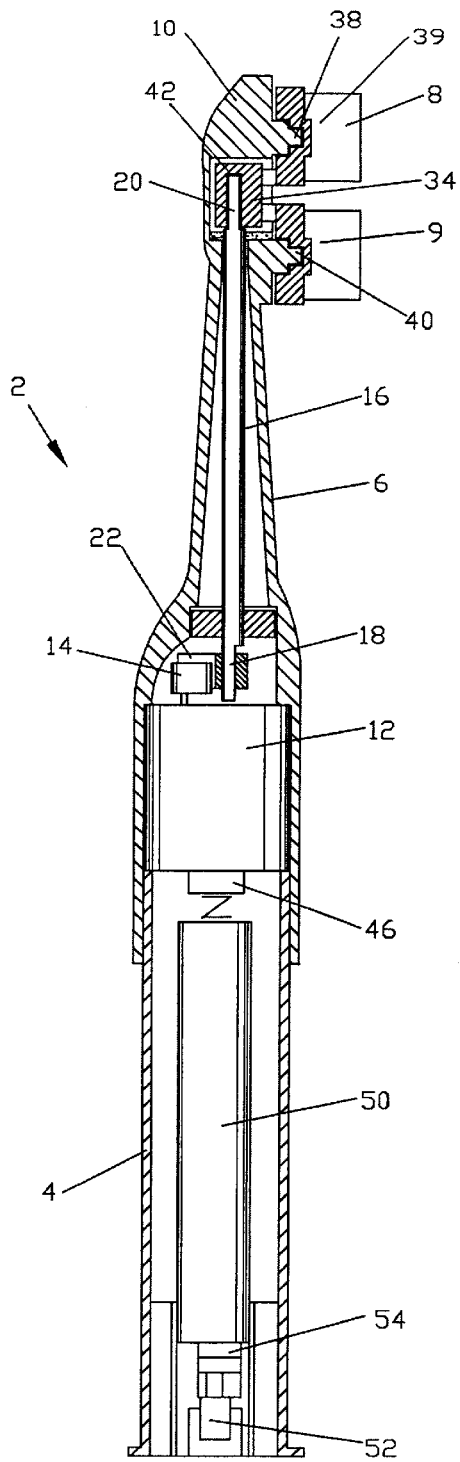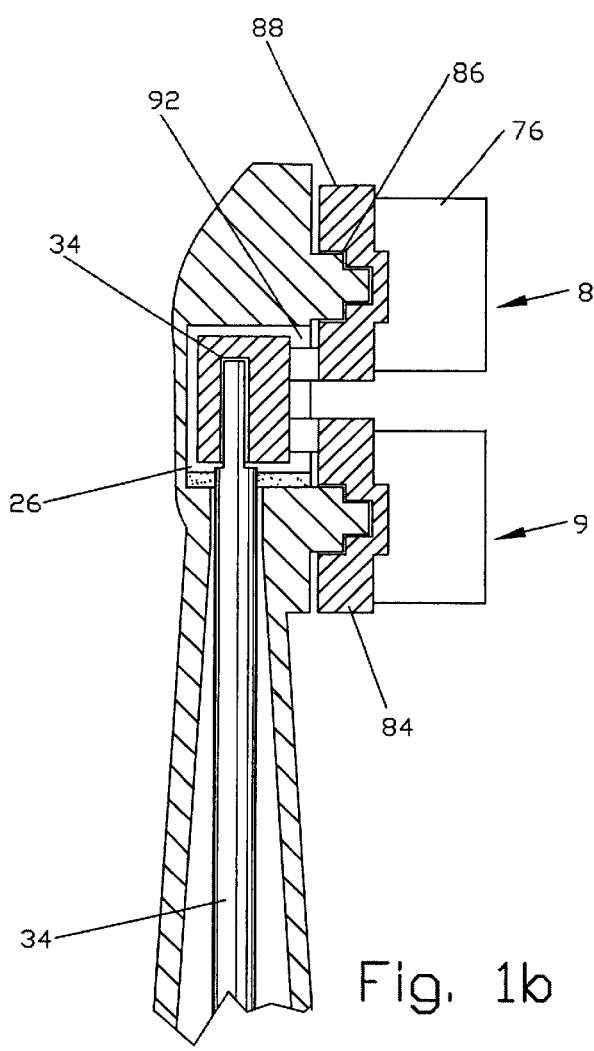
Fig. 1a
Fig. 1b

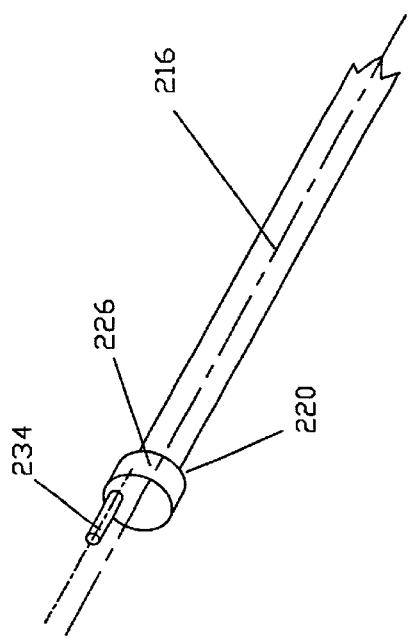
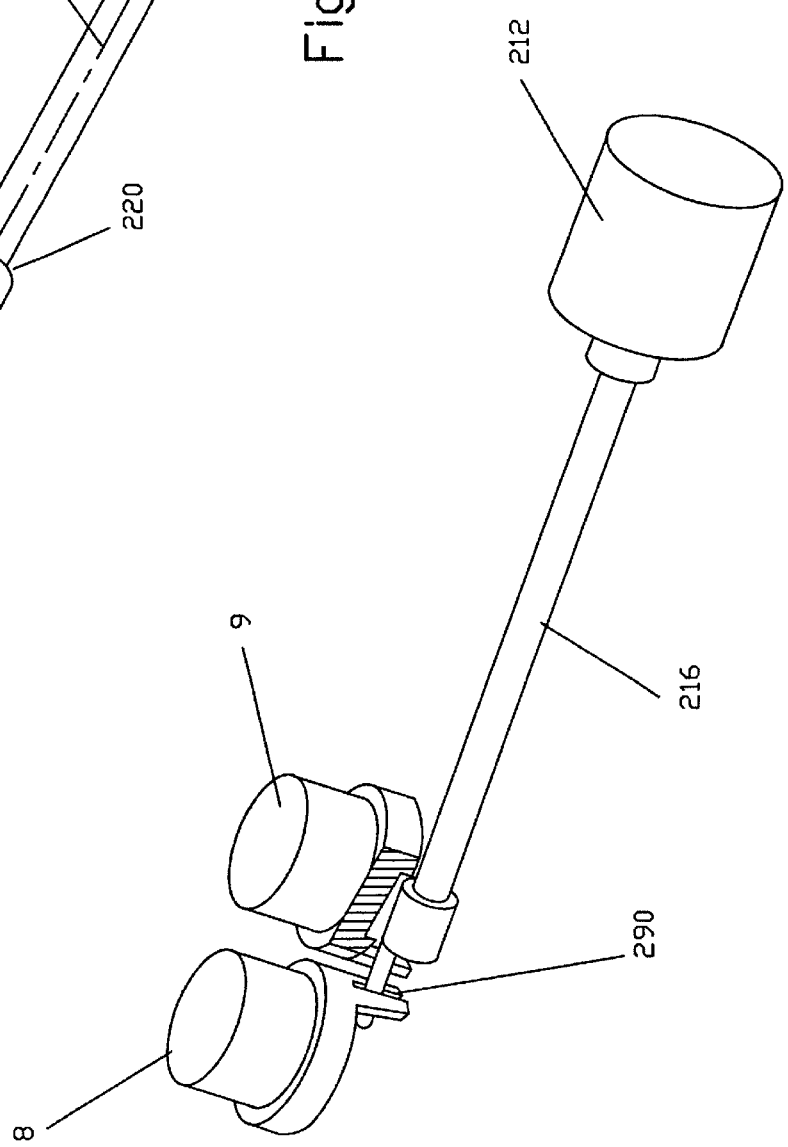

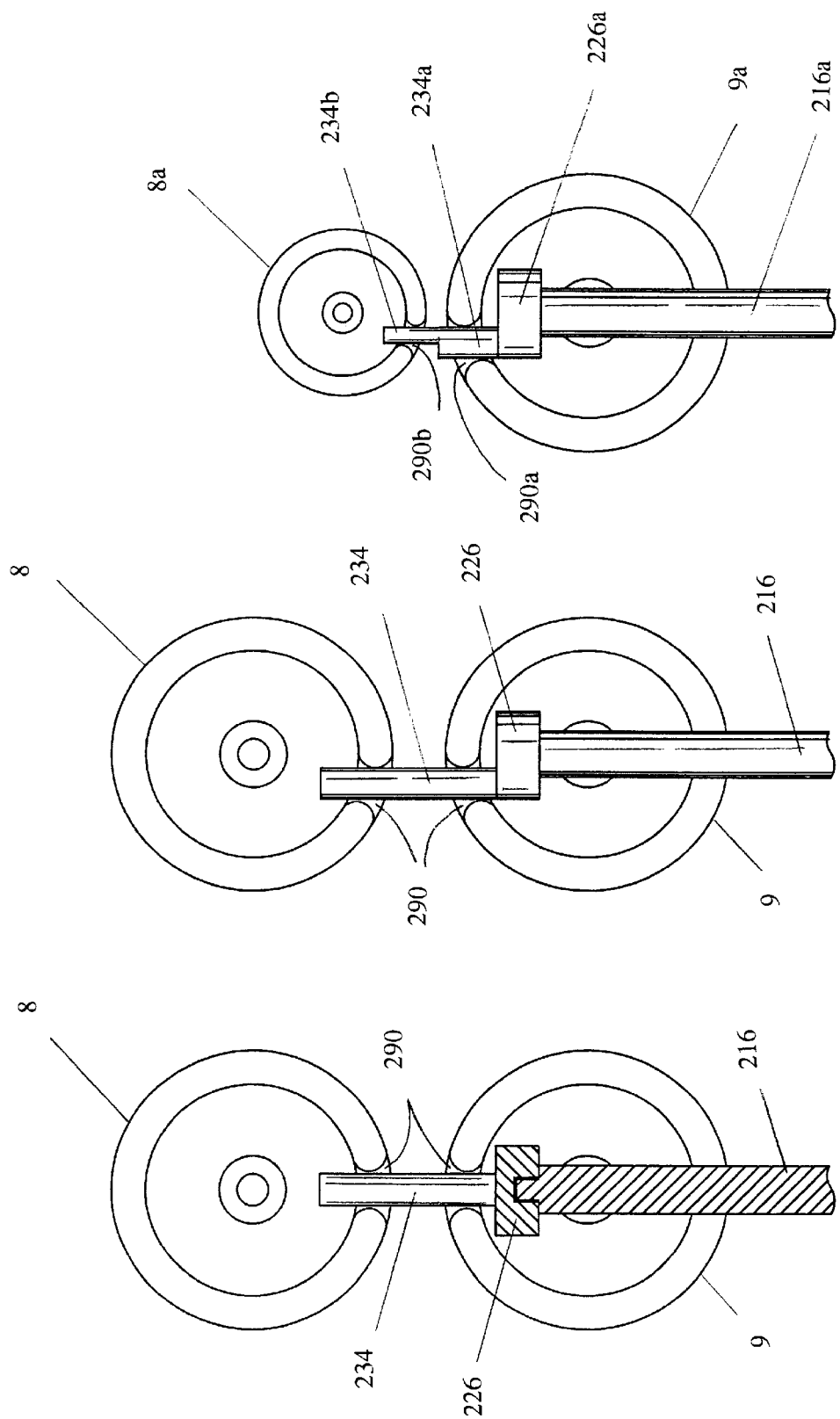

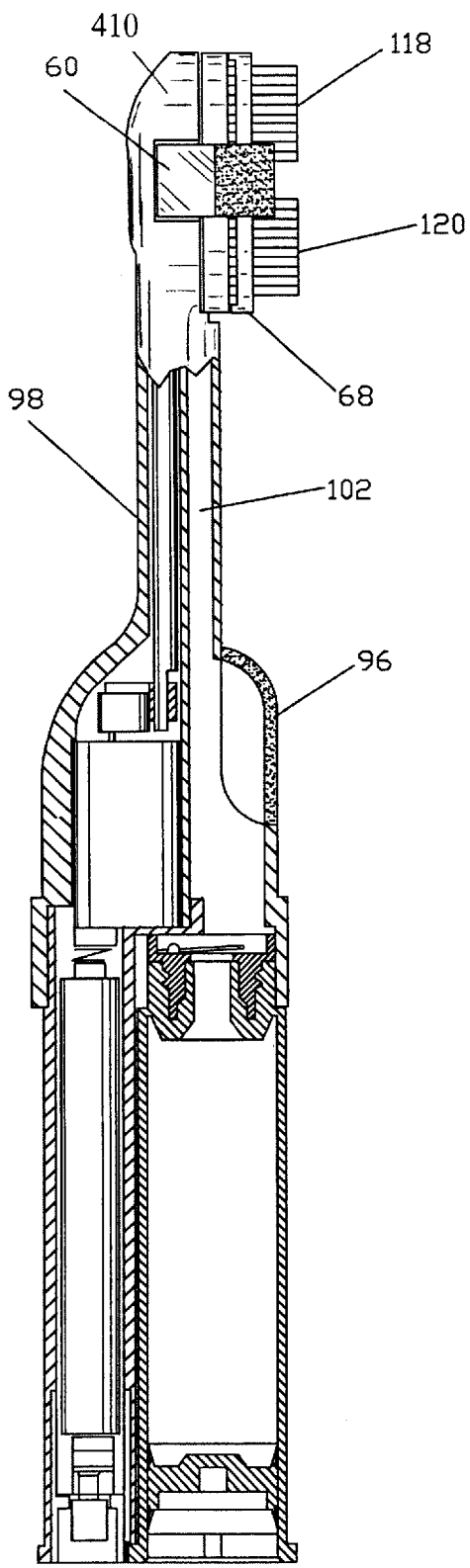
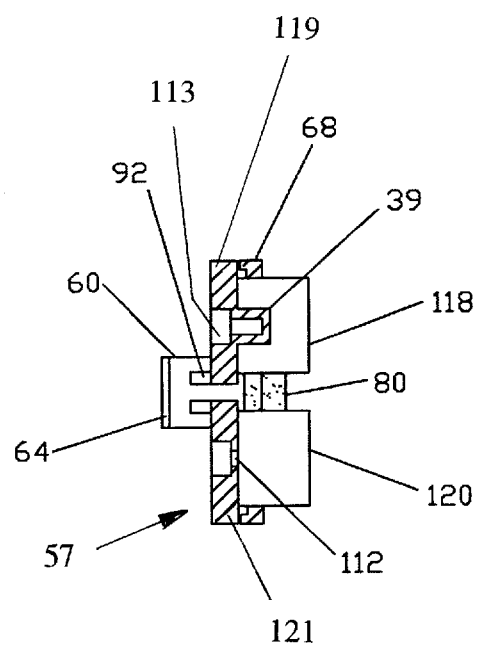
Fig. 6a
Fig. 6b

DENTIFRICE DISPENSING ELECTRICAL TOOTHBRUSH WITH SNAP-ON DUAL BRUSH UNIT

BACKGROUND OF THE INVENTION

It has been recognized through clinical tests that an electrical toothbrush is more effective in removing plaque and preventing gum disease than a conventional manual toothbrush. It is also well known that toothbrush bristles should be replaced on a regular basis since bristle harbor germs after a period of use. While the entire toothbrush can be replaced, it is more economical to replace only the brush elements. In order for an electrical toothbrush to have wide acceptability, the time required to accomplish the brushing operation and the cost required to replace the brush head must be less than that of a manual toothbrush. To obtain the equivalent brushing area of a conventional toothbrush, it is desirable to utilize an electrical toothbrush which has two oscillating brush elements. It is also desirable to replace only the bristle elements and retain the neck portion of the electrical toothbrush for permanent use to minimize replacement costs. And for ease of replacement, it is desirable to have a snap-on feature for self-locating the replaceable bristle elements on the brush head. For the convenience of portability, it is desirable to have a self contained, dentifrice dispensing electrical toothbrush for brushing anywhere at anytime. For the ease of operation of persons with disabilities such as one-handed persons and arthritis sufferers, it is desirable to have a single push-type button to dispense dentifrice material in a controlled quantity and to simultaneously activate a motor which oscillates the brush heads for a pre-determined period of time for brushing. The objects of The objects of this invention are to achieve all of the above desirable features in one electrical toothbrush.

(1) Field of the Invention

The present invention relates to electrical toothbrushes with replaceable brush elements.

(2) Prior Art

It is recognized in the prior art that electrical toothbrushes which have oscillatory brush elements are more effective than toothbrushes with rotating brush heads. The reciprocating movement and wiping action of the bristles provides an effective means for plaque removal. U.S. Pat. No. 4,326,314 by Moret and Jousson describes a means for oscillating a brush head through an oscillating shaft which is connected to a cam riding on a biased wheel mounted on the shaft of a motor. Since the source of vibration is at the cam and the motor which are usually located in the handle, a strong vibration may cause discomfort during brushing.

To minimize the vibration at the handle, U.S. Pat. No. 5,625,916 by McDougall provides a means for converting rotary motion to oscillatory motion near the brush head area which is remote to the motor. It uses a bent remote-most end of a shaft having rotary motion to engage with a slot formed on the side of a bristle holder to force it to oscillate back and forth as the bent remote-most end is driven in a circular annular path. While it achieves relocation of the vibration source to the brush head, the central axis of the bent remote-most end is required to intersect with the central axis of the brush head. This requirement precludes its application for simultaneously driving two brush heads since the same central axis of the remote-most end of a shaft cannot intersect two separate central axes in its circling positions. Also, its use of a closed ended slot on the side of the brush head for engagement also prevents the remote-most end from reaching more than one brush head. Owing to its complex assembly, the entire neck including the brush head, the mounting base and the drive shaft assembly are replaced when the brush head is changed.

U.S. Pat. No. 5,784743 by Shek uses an off-set finger mounted at the end of a rotating shaft for engaging the fork of a pivotally supported wobble plate which is meshed with a gear for oscillating a brush head. The use of the closed end fork and the blocking of the extension of the finger by the pivoting and gear-meshing mechanism prohibit its application to oscillate two brush heads. Similarly, the replacement of the whole neck including the drive shaft is required when the brush head is replaced.

The prior art has also recognized that the brushing area is broadened and the brushing time reduced when two brush heads are used instead of one. For oscillating two brush heads, U.S. Pat. No. 5,353,460 by Bauman uses an oscillating shaft to drive one brush head and utilizes a linkage between the two brush heads to drive the other brush head. The linkage requires a pivoting post on each brush head which adds an increased friction load to the drive mechanism for oscillation of the brush heads. U.S. Pat. No. 5,099,536 by Hirabayashi uses two shafts aligned at different angles. The gearing mechanism allows for driving more than one brush head but its drive mechanism does not cause oscillatory motion. In order to change the brush head, each of the above two patents also requires replacing the neck connected to the brush head which includes part of a drive shaft assembly.

A description of an electrical toothbrush which dispenses liquid is provided in U.S. Pat. No. 5,321,866 by Klupt. The patent discloses a delivery means for a cleaning liquid through oscillating brush heads. A motor is connected to a series of gear mechanisms for causing a drive shaft to oscillate and a piston to pump the liquid through a flow conduit to openings in the brush head. Because it is connected to the same motor, the motorized piston pumps the liquid continuously while the brush heads are oscillating. This common drive mechanism is not desirable for dispensing material that only needs to be dispensed prior to the brushing action.

SUMMARY OF THE INVENTION

This invention provides an electrical toothbrush that satisfies the need for high cleaning efficiency and snap-on replacement parts for easily replacing brushing elements. It also provides a dentifrice dispensing electrical toothbrush that meets a need for simplicity of operation with a single push-button action for both dispensing dentifrice material and energizing a motor for oscillating the brushing elements. The electrical toothbrush of the invention uses a drive mechanism that causes oscillation of two independent brush elements for accomplishing effective cleaning in less time. Rotary motion from a motor is converted to oscillatory motion with either a cam assembly or an off center shaft extension for engaging the drive notches on the brush elements. The brush elements, each of which has plurality of bristles attached to a platform, are mounted on stationary posts on a brush head in a manner that allows them to freely oscillate. They are easily detached and replaced without replacing other components in the drive mechanism. The brush elements are positioned in a retention cradle which facilitates their installation and removal. The retention cradle is detachably positioned on the brush head using a snap-on feature. This feature includes a pair of opposing resilient tabs built on the retention cradle for deflecting a corresponding pair of fastening arms. The fastening arms are lockable on the brush head base and are released by applying an opposing force on the tabs. The resilient tabs are positioned below the bristle surface and are optionally layered with rubber material for protecting gums from excessive brushing pressure.

In dentifrice dispensing toothbrushes, the dual brush elements and the driving mechanism of this invention enable the dispensing of dentifrice material to one of the brush elements which distributes the dentifrice material to all brushing areas during brushing action. The delivery of the dentifrice material is achieved by using a toothbrush neck having two separated channels. One channel houses the drive shaft and the other channel functions as part of the flow path for the dentifrice material as it is pumped from the handle to the brush head. The pumping mechanism includes a refillable cartridge, a one-way valve, a pumping chamber and a resilient compressible button for applying pressure to force dentifrice material from the chamber to the top of the brush element. The brush element has an opening in its base which allows it to be slidably mounted on the wall of a spout opening extending from the top of brush head base. An internal switch covered by a resilient membrane is located inside the pump chamber. The switch is activated by the hydrostatic pressure created by pressing on the resilient compressible button for pumping dentifrice material from the pump chamber. A motor and a timer are simultaneously activated when the internal switch is activated. The timer controls the running time of the motor that energizes the brush elements.

The essential components of the electrical toothbrush include 1) a handle which serves as a housing for a motor, batteries and a cartridge containing dentifrice material; 2) a brush head with two posts extending from its top surface; 3) a neck which connects the handle and the brush head; 4) two brush elements, each having a notch on its side wall, and each having a plurality of bristles attached to its top surface and a circular recess in its bottom surface for detachable mounting on the post; 5) a drive mechanism that is driven by a motor and imparts an oscillatory motion to the brush elements by engagement with their side wall notches; and, 6) a snap-on cradle having deflectable arms for mounting the brush elements on the posts of the brush head base in a freely rotatable position, and having resilient tabs for disengaging the cradle from the brush head base. The electrical dentifrice dispensing toothbrush also includes 7) a pumping mechanism including a pump chamber, a one-way valve and a resilient compressible button; 8) a refillable dentifrice cartridge; and, 9) a cover with a slidable sealing plug for insertion into the spout opening to prevent drying of the dentifrice material in the flow channel.

In accordance with the invention, the retention cradle is also used with a toothbrush having a single brushing element. The drive system and retention cradle are not only used in electrical dentifrice dispensing toothbrushes, but they are also used in standard electrical toothbrushes which do not have dentifrice dispensing capabilities.

BRIEF DESCRIPTION OF THE DRAWINGS

FIG. 1a is a cross section view of a drive mechanism for a dual-headed electrical toothbrush FIG. 1b is an enlarged cross section side view of the drive mechanism shown in FIG. 1a.

FIG. 2f is a perspective view of a drive shaft.

FIG. 2g is a perspective view of a draft shaft engaged with brush elements.

FIGS. 2h and 2i are bottom views of the engagement of a drive shaft element with brush elements which are the same size shown in FIG. 2g.

FIG. 2j is a bottom view of the engagement of a drive shaft element with differently sized brush elements.

FIG. 4a is a side cross section view of a dentifrice dispensing electrical toothbrush.

FIG. 4b is a cross section view along 4b—4b of the toothbrush shown in FIG. 4a

FIG. 5a is a side cross section view of an electrical toothbrush with brush elements removed.

FIG. 5b is a pirtial cross section along 5b—5b of the electrical toothbrush shown in FIG. 5a.

FIG. 6a is a side view of an electrical toothbrush with snap-on brush elements mounted.

FIG. 6b is a cross section view of the brush elements of the toothbrush of FIG. 6b.

DETAILED DESCRIPTION OF PREFERRED EMBODIMENTS

Figure 2B:
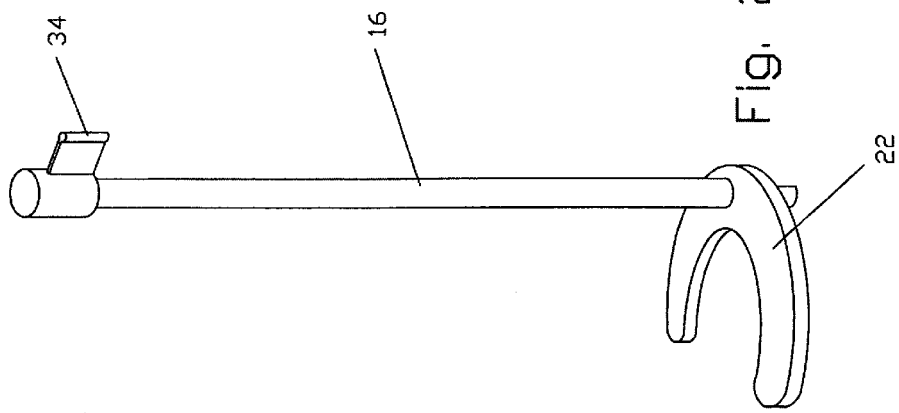
FIG. 2b is a perspective view of drive shaft with end cap attached.
Figure 2A:
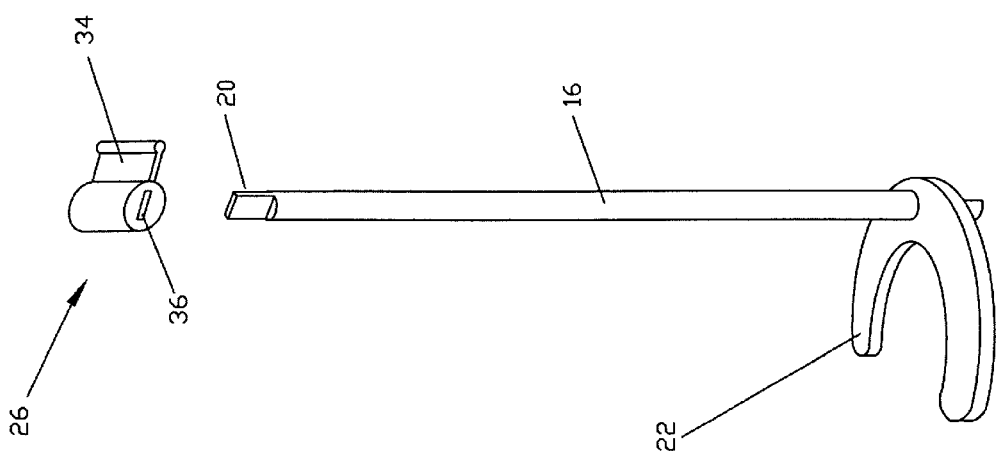
FIG. 2a is a perspective view of a drive shaft and end cap.
Figure 2C:
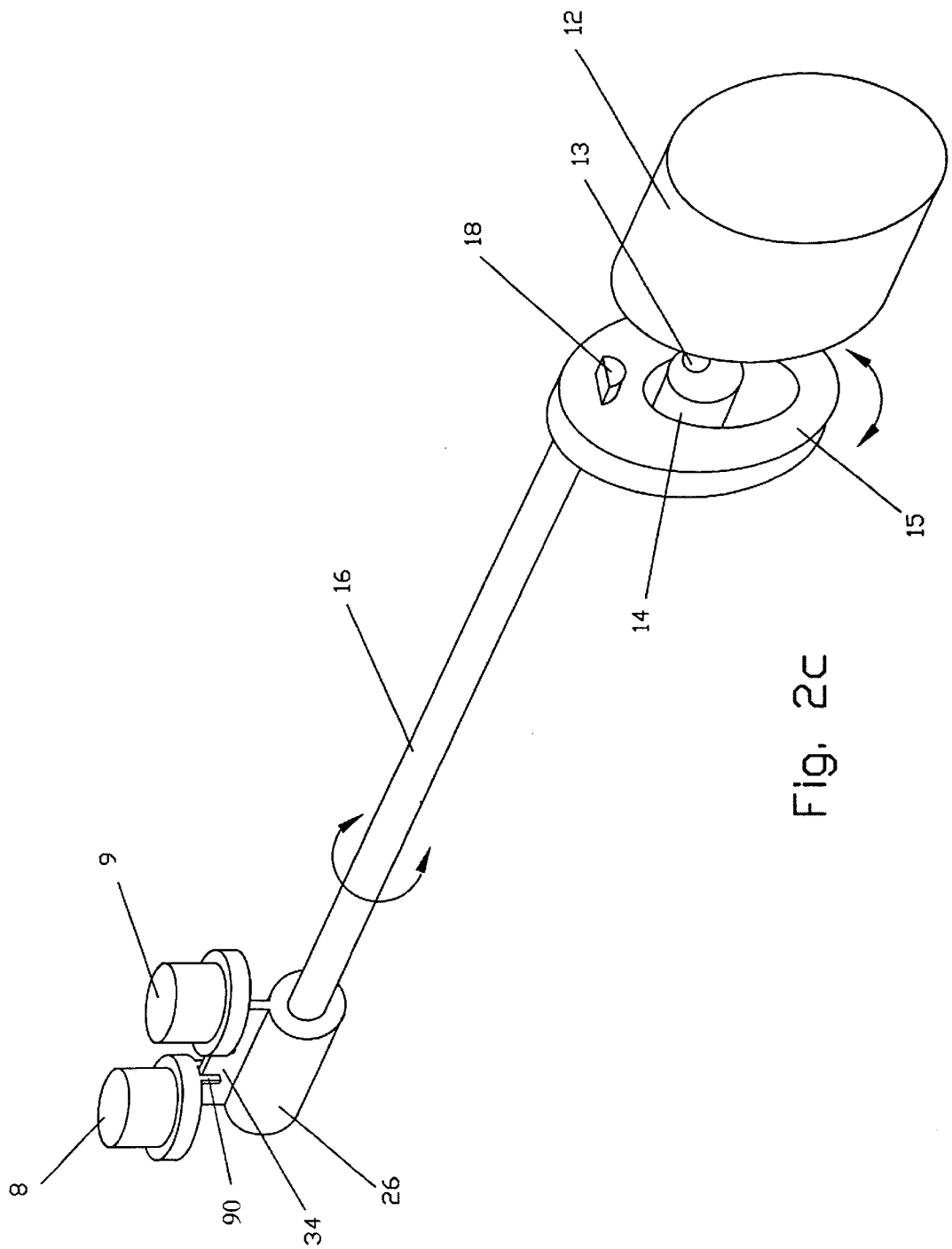
FIG. 2c is a perspective view of a drive shaft with an oval-shaped cam.
Figures 2D, 2E:
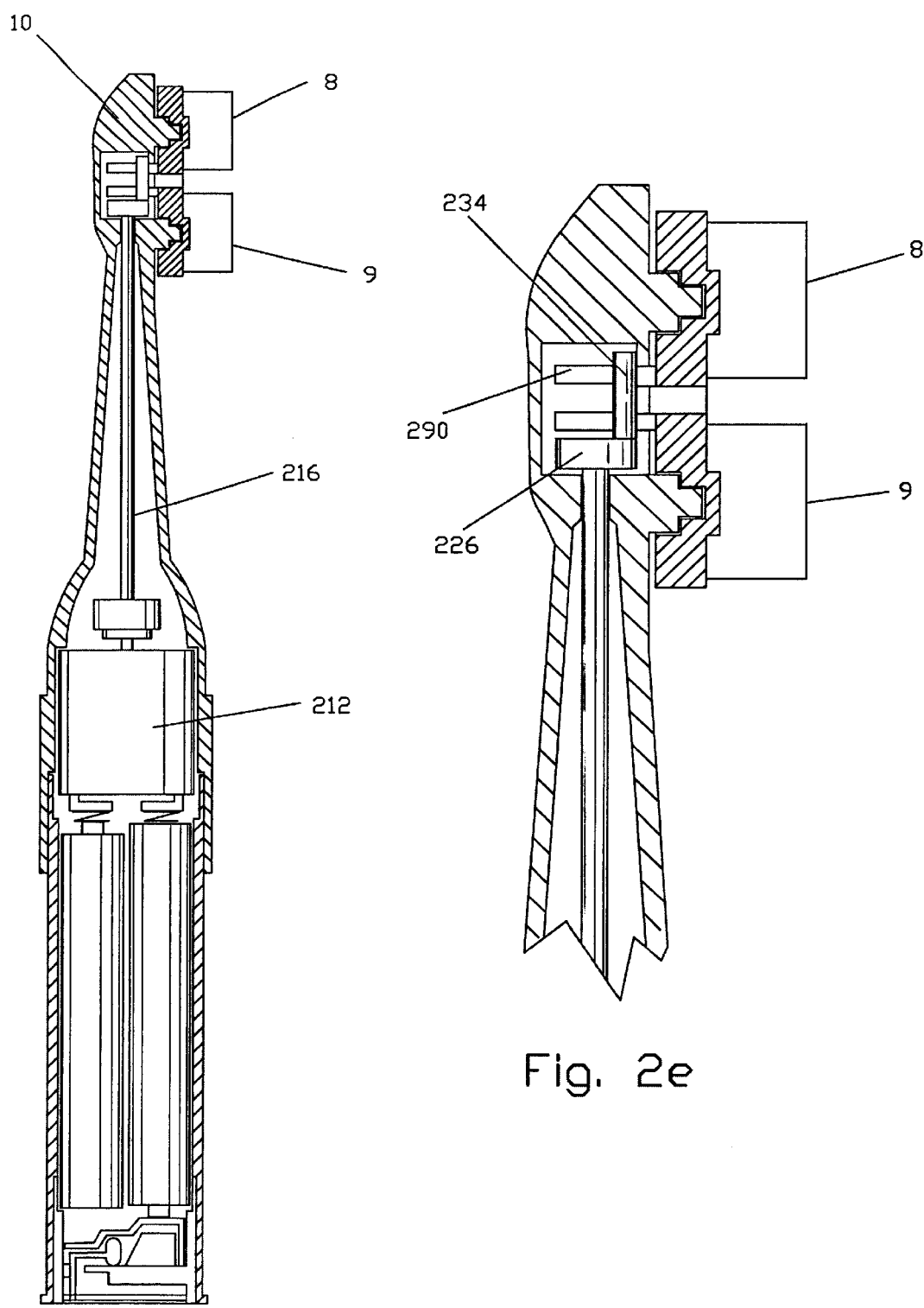
FIG. 2d is a cross section view of a drive mechanism with a cylindrical rod.
FIG. 2e is an enlarged cross section view of the drive mechanism shown in FIG. 2d.

FIG. 1a shows a toothbrush 2 having a handle 4 and a brush head 10 connected by neck 6. Replaceable brush elements 8 and 9 are detachably mounted on posts 38 and 40 which extend from brush head 10. Motor 12 and batteries 50 are positioned within handle 4. Leaf spring contact 54 is situated at the end of battery 50 and switch 52 extends through an opening in the base of the handle. Batteries 50 are connected to motor 12 by contact 46. Drive shaft 16, having a central longitudinal axis, is positioned in neck 6. Drive shaft 16 and motor 12 are connected by a cam assembly as shown in FIGS. 2a, 2b and 2c which imparts an oscillating motion to the drive shaft. Motor 12 drives bias wheel 14 which is connected to motor output shaft 13. A U-shaped cam 22 (FIGS. 2a and 2b) or an oval-shaped cam 15 is connected to end 18 of drive shaft 16. Cap 26 is attached to remote end 20 of drive shaft 16 by insertion of end 20 in recess 36 at the base of the cap. Tab 34 extends radially outward from the central longitudinal axis of drive shaft 16. When connected to drive shaft 16 as shown in FIG. 2b, tab 34 oscillates with drive shaft 16. As explained below, tab 34 in turn imparts its oscillating motion to brush elements 8 and 9 which increases brushing efficiency.

Figure 3C:
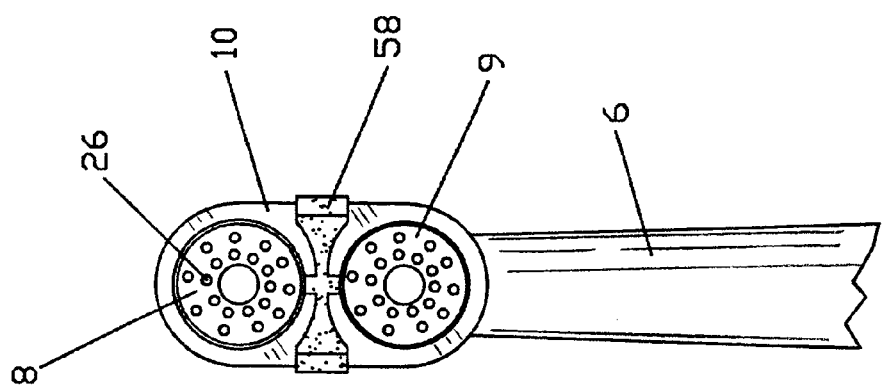
FIG. 3c is a front view of an electrical toothbrush with a snap-on brush retention cradle mounted on a brush head.
Figure 3B:
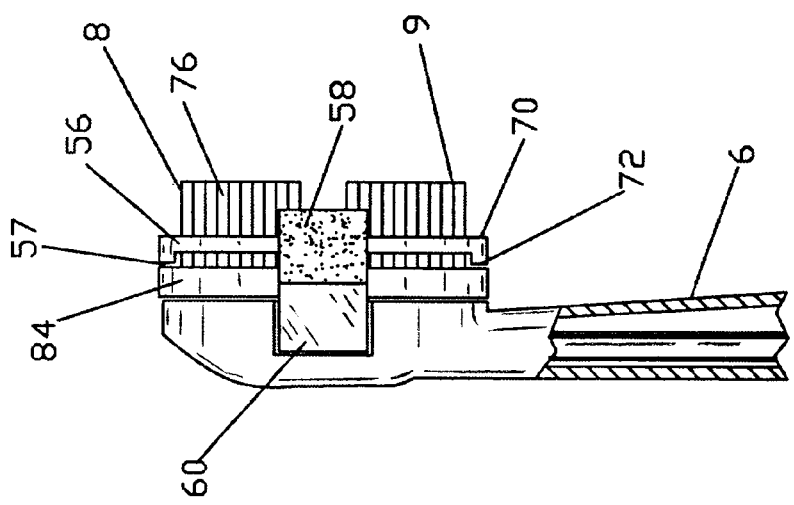
FIG. 3b is a side view of an electrical toothbrush with a snap-on brush retention cradle mounted on a brush head.
Figure 3A:
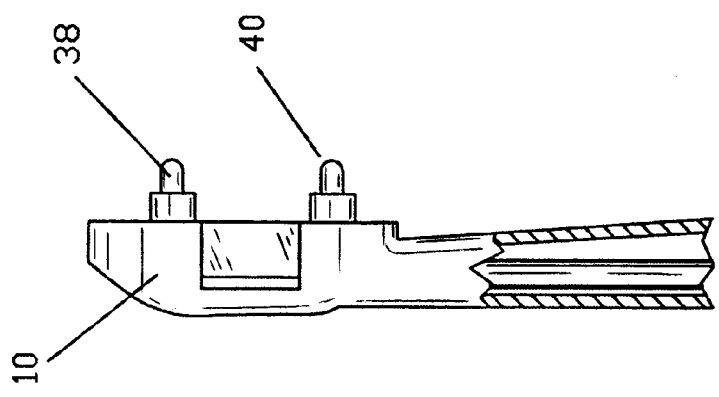
FIG. 3a a cross section side view of dual-headed electrical toothbrush with brush elements removed.
Figure 3G:
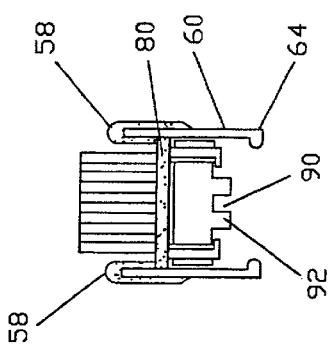
FIG. 3g is a cross section view along 3g—3g of FIG. 3f.
Figure 3F:
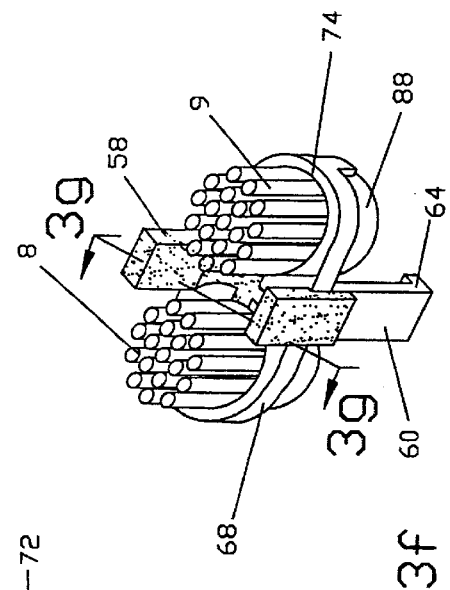
FIG. 3f is a perspective view of a retention cradle with brush elements.
Figure 3E:
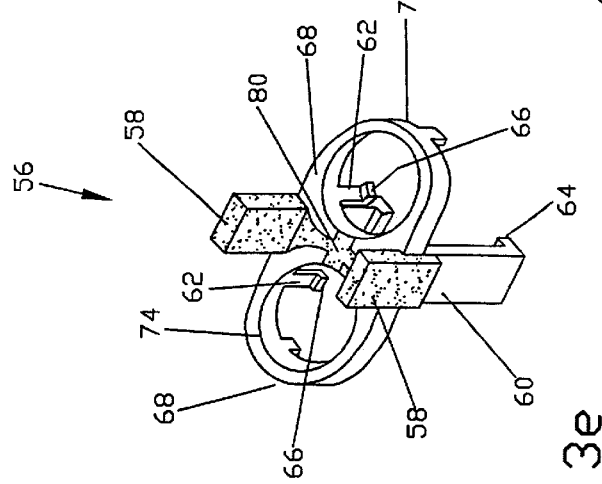
FIG. 3e is a perspective view of a snap-on retention cradle.
Figure 3D:
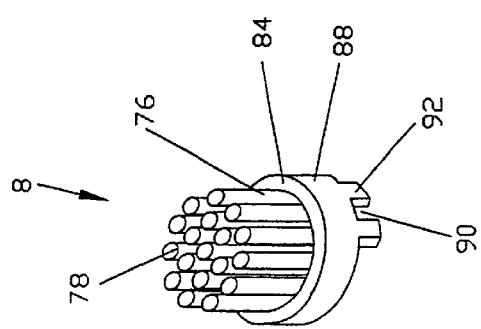
FIG. 3d is a perspective view of a brush element.

As shown in FIGS. 1b and 3d, a plurality of bristles 76 are attached to the top surface of platform 84 of brush element 8. The free ends of bristles 76 form brush surface 78. Extension 92 with notch 90 is appended to side wall 88 of platform 84. The underside of platform 84 has a recess 86 which is shaped to mate with posts 38 and 40 of brush head 10. Notch 90 of brush elements 8 and 9 accommodates tab 34 such that when tab 34 is positioned in notch 90, the oscillating motion of tab 34 causes brush elements 8 and 9 to freely oscillate on posts 38 and 40.

Figure 3I:
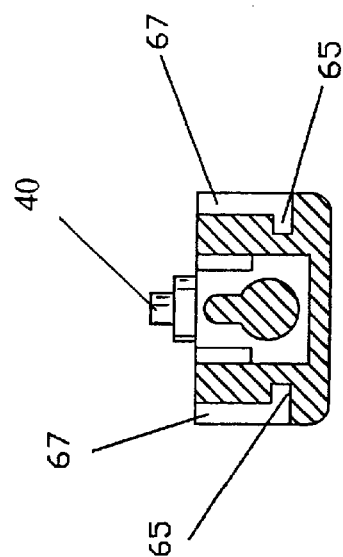
FIG. 3i is a cross section view along 3i—3i of the brush head shown in FIG. 3h.
Figure 3H:
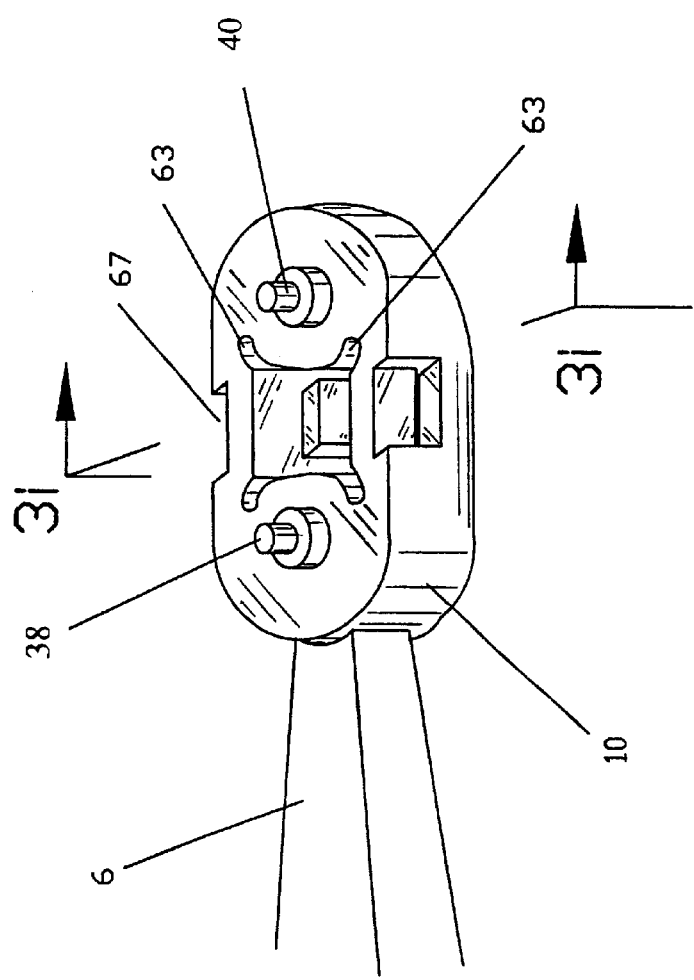
FIG. 3h is a perspective view of a brush head.

Brush elements 8 and 9 are held in position by retention cradle 56 as shown in FIGS. 3d, 3e, 3f and 3g. Retention cradle 56 is attachable to and detachable from brush element platform 84 which permits the removal and replacement of brush elements 8 and 9. Retention cradle 56 includes platform 68 with two openings defined by retention rims 74. A pair of opposing arms 60 extends from the bottom of platform 68 and the remote end of each arm has an inward extending rib 64 which detachably engages recess 65 in brush head 10 with arms 60 positioned in grooves 67 in brush head 10 (FIGS. 3h and 3i). A pair of opposing tabs 58 extend from the top surface of platform 68. Portions of tab 58 overlap portions of arms 60 and are configured in a manner such that inward deflection of tabs 58 toward each other causes outward deflection of opposing arms 60 and their disengagement from brush head 10. A pair of opposing deflectable catch arms 62 having inwardly opposing ribs 66 at their remote ends also extend from the bottom surface of platform 68. Ribs 66 retain brush elements 8 and 9 in rim 74 when retention cradle is disengaged and removed from brush head 10.

The diameter of each retention rim is larger than the diameter of the outer perimeter of bristles 76 of the element positioned therein but smaller than the diameter of the brush element platform 84 supporting the bristles. This configuration prevents dislodgment from the top side of the retention cradle. Also, catch arms 62 and ribs 66 prevent dislodgment of the element from the bottom side of the cradle. The length of the catch arm facilitates its deflection and the inwardly toed ribs are positioned to support the bottom of the brush element. The brush element is forced into place from the bottom side of the retention cradle by the outward deflection of the catch arm ribs. When framed in place in the retention cradle, the brush elements are maintained in a free-to-rotate position. The bottom surfaces of the retention rims optionally include a plurality of spacing elements to create a gap between the bottom surfaces of the rims and the top surface of the brush head to allow for the passage of water there through.

After the brush elements are placed in the retention cradle, it is mounted on the brush head and secured in place using the snap-on features described above. As shown in FIGS. 3h and 3i, the fastening arms are positioned to slide downwardly on the guide grooves 67 on opposite side walls of the brush platform 10 and latch into recess 65. Catch arms 62 of retention cradle 56 are accommodated by the catch arm recesses 63 in the top surface of brush head 10. When the retention cradle is fastened in position, there is clearance between the top surface of the brush head and the bottom surfaces of the retention rims to enable free oscillation of the brush elements on posts 38 and 40. The arms and ribs are readily fabricated as integral parts of the retention cradle by the plastic injection molding process. Because of the small protrusions of the ribs from the walls, the retention cradle is directly ejected, in tact, from the mold cavity at elevated temperatures with the arms and ribs being resiliently deflected in a side direction.

To increase the flexibility of the retention cradle, opposing local segments on a symmetrical plane on the edge of each retention rim is co-injection molded with rubber material. As shown in FIG. 3g, rubber segments are integrated with a rubber layer 80 across the center portion of the retention cradle. The rubber layer is extended over the surface of the two tabs including the top ends 58. The soft rubber on top of the tabs guards the user's gums against brushing at excessive pressure and improper angles as described in co-pending application Ser. No. 09/633733 of Kuo. In order to accomplish this purpose, the height of the tabs is below the free surface 78 of the bristles. The precise height is dependent on the allowable maximum brushing pressure and the rigidity of the bristles.

Figure 3J:
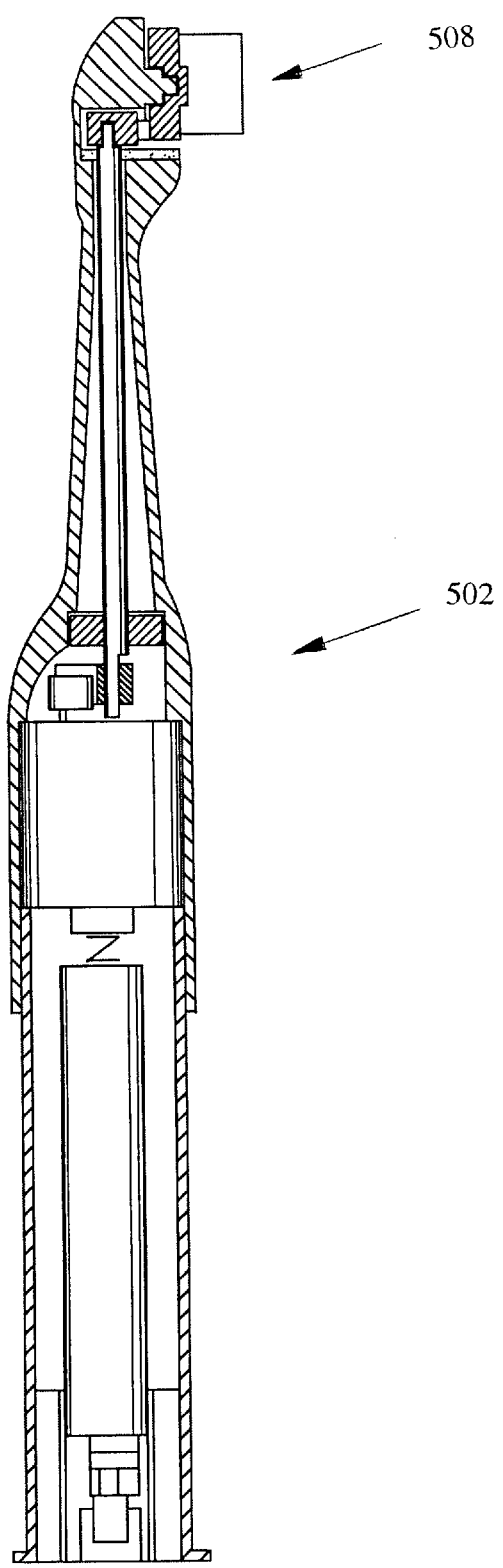
FIG. 3j is a cross section side view of a drive mechanism for a single brush element electrical toothbrush FIG. 3k are perspective views of a snap-on single brush element assembly.
Figure 3K:
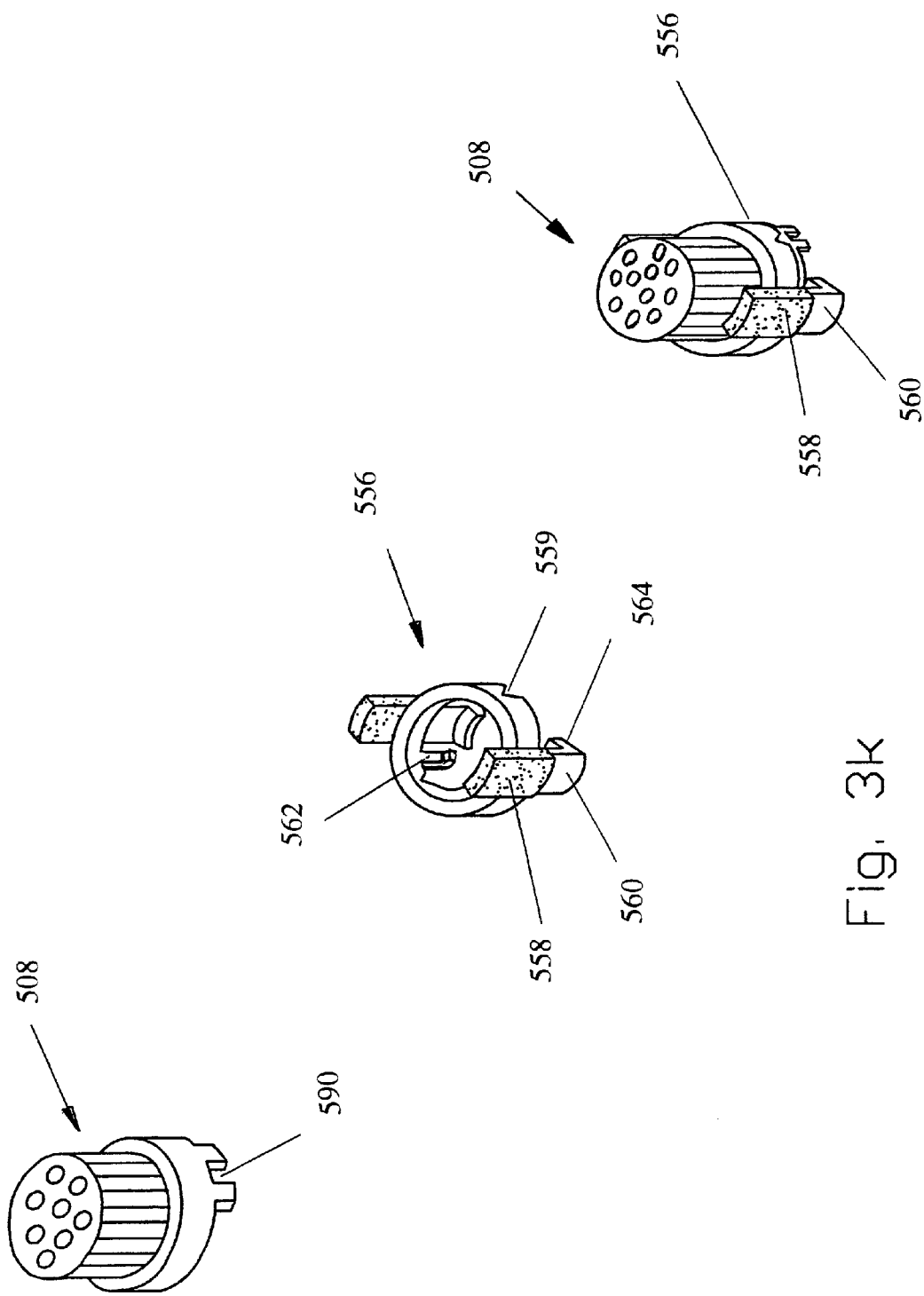

The snap-on retention cradle used to facilitate the replacement of the brush elements on dual headed electrical toothbrushes, is also used to facilitate replacement of the brush elements on electrical toothbrushes having a single element. FIG. 3j shows the engagement of a drive mechanism, which is similar to that shown in FIG. 1a, with the drive notch of a single brush element. FIG. 3k shows the snap-on assembly of a single brush element 508 with retention cradle 556 which has catch arms 562 for preventing the brush element from bottom side dislodgment. Fastening arms 560 with ribs 564 are used to engage the recesses in the side walls of the brush head in a fastening position that allows free rotation of the brush element. To facilitate the deflection of the opposing tabs 558 for disengaging ribs 564 from the brush head, the bottom surface of retention cradle 556 has opposing v-notches 559 positioned perpendicular to opposing tabs 558 such that the notched areas function as a living hinge. The elastic nature of v-notches 559 enables the retention cradle to fully recover to its original shape as the opposing deflection forces on opposing tabs 558 are released.

FIGS. 2d, 2e, 2f and 2g show another embodiment for imparting oscillating motion to brush elements 8 and 9. In this embodiment, drive shaft 216 is directly coupled to motor 212. Cap 226 is attached to remote end 220 of drive shaft 216. Cylindrical rod 234 is attached to cap 226 in a manner such that the central longitudinal axis of cylindrical rod 234 is parallel to and offset from the central longitudinal axis of drive shaft 216. Cylindrical rod 234 is mateable with notches 290 of brush head elements 8 and 9. Rotation of drive shaft 216 and cap 226 cause movement of cylindrical rod 234 in notches 290 in a manner that it imparts an oscillating motion to brush elements 8 and 9. In this embodiment, a cam assembly, such as that shown in FIG. 1a, is not necessary.

The drive mechanism described herein is suitable for imparting an oscillating motion to two brush elements that are the same size and are structurally identical. The configuration of the drive mechanism for such identically structured brush elements is detailed in FIGS. 2b and 2c which show the engagement of tab 34 with notches 90 in brush elements 8 and 9. In this engagement, the notches of the two brush elements face each other with tab 34 positioned in each notch. When the motor is energized, the rotation of biased wheel 14 causes U-shaped cam 22 to move back and forth as it follows the eccentric motion of the biased wheel. The reciprocating motion of the U-shaped cam causes tab 34 and brush elements 8 and 9 to oscillate accordingly, each brush element being independently driven by tab 34. A closed oval-shaped cam 15 which has its inner wall in sliding contact with the biased wheel, as shown in FIG. 2c, is used in place of U-shaped cam 22 in situations where additional structural rigidity is required.

The drive mechanism shown in FIGS. 2d, 2e, 2f, 2g, 2h and 2i is also suitable for imparting oscillating motion to a pair of similarly structured brush elements but produces less handle vibration because a cam and biased wheel are not directly connected to the motor. Since there is no cam and biased wheel in the handle area, the drive shaft rotates in only one direction rather than in a reciprocal manner. The positioning of notches 290 of brush elements 8 and 9 in relation to each other in their engagement with cylindrical rod 290 is detailed in FIGS. 2h and 2i. The notches are formed by the extensions of the side walls of the brush elements. The length of a side wall extension is sufficient to enable the inner surface of the notch in the extension to remain in contact with the cylindrical rod during a full 360 degree rotation of the drive shaft. The width of notches 290 is the same as the diameter of cylindrical rod 234. The inner surfaces of the notches are rounded to reduce friction and minimize the clearance between the cylindrical rod and the notches. In operation, shaft 216, which is connected directly to the motor, drives cap 226 which causes cylindrical rod 290 to rotate in an annular path. Due to the close engagement of the cylindrical rod with the notches of the brush elements, the cylindrical rod forces the side wall extensions of the brush elements to move accordingly. A full circle movement of the cylindrical rod causes a full backward and forward cycle of oscillation of the brush heads. An advantage of this arrangement is that it relocates the source of the oscillatory motion away from the handle and closer to the brush head.

The drive mechanism shown in FIG. 2j is particularly suitable for driving brush elements which are not identical. This allows two differently sized brush elements, 8a and 9a, to be separately mounted and driven on the same brush head. This configuration enhances brushing efficiency since the smaller brush element reaches areas of the teeth that are not accessible by the larger brush element. In FIG. 2j, cylindrical rod 234a is attached to cap 226a in a manner such that the central longitudinal axis of cylindrical rod 234a is parallel to and offset from the central longitudinal axis of drive shaft 216a. The diameter of cylindrical rod 234a matches the width of notch 290a in the side wall of brush element 9a. A second cylindrical rod 234b having a diameter smaller than that of cylindrical rod 234a, is attached to cylindrical rod 234a in a manner such that the central longitudinal axis of cylindrical rod 234b is offset from the central longitudinal axis of cylindrical rod 234a. The diameter of cylindrical rod 234b matches the width of notch 290b in the side wall of smaller brush element 9b. In operation, brush elements 8a and 9a have the same frequency of oscillation even though they are different sizes and driven by a common drive shaft.

Because the end cap and the drive shaft are separate components, the drive mechanism described herein is characterized by ease of assembly and reliability of operation. In a manufacturing process, the end cap is first seated in the recess of the brush head with the tab or cylindrical rod positioned toward the top surface of the brush head. Then the drive shaft is inserted through the neck so that the flat surface (D-shaped or an equivalent non-circular cross section shape) at the end of the drive shaft extends beyond the opening at the end of the neck. The end of the drive shaft is inserted into the receptacle on the bottom surface of the end cap. The entrance to the receptacle is chamfered to facilitate insertion. The local area around the neck opening is made water proof by co-injection molding with a rubber material on top of a primary material on the neck and brush head. The rubber material used provides a sealing function for the sliding fit of the shaft with the neck which prolongs the use of the drive mechanism.

The invention described herein is also applicable to a dentifrice dispensing toothbrush such as that shown and described in U.S. Pat. No. 5,909,977 by Kuo. In accordance with this embodiment, toothbrush 402, as shown in FIGS. 4a, 4b, 5a and 5b, has handle 404, neck 406 and brush elements 408 and 409 mounted on posts 106 and 108 of brush head 410. U-shaped cam 22 is positioned between one end of drive shaft 416 and motor 412. Cap 426 with tab 434 is attached to the remote end of drive shaft 416. Motor 412 is powered by battery 450 which is stored in handle 404. Dentifrice containing cartridge 124 having follower 126 is also housed within handle 404. Dentifrice material is pumped from pump chamber 94, through channel 102 and spout opening 114, to brush element 409. A pumping force is supplied to chamber 94 by depression of elastic compressible button 96. The vacuum created in chamber 94 when the pumping force is discontinued and elastic compressible button 96 is restored to its original position, causes dentifrice material to flow from cartridge 124 through one way check valve 122 and into chamber 94 to replace the quantity of dentifrice material removed from the chamber by the application of the pumping force. The flow of dentifrice material from cartridge 124 causes corresponding advancement of follower 126 at the base of the cartridge. As shown in FIG. 5a, neck 98 has two chambers which are separated by a partition. Channel 100 contains the drive shaft while channel 102 provides the flow path for dentifrice material from the pump chamber to the brush elements.

As shown in FIG. 5a, post 106 of brush head 410 is solid while post 108 is hollow and terminates at opening 114 to form spout 115. The outer wall of spout 115 is part of post 108. The retention cradle 57 shown in FIG. 6b is detachably secured to brush head 410 of FIG. 6a by fastening arm 60 and rib 64. Brush elements 118 and 120 are positioned in openings in retention cradle platform 68. The underside of platform 119 of element 118 has a recess 113 which is shaped to mate with solid post 106. Platform 121 of brush element 120 has an opening 112 which extends through the platform and is shaped to mate with hollow post 108. When the retention cradle and brush elements are mounted on brush head 410, opening 112, spout 115 and channel 102 are aligned to provide a continuous path for dentifrice material to flow from chamber 94 to the bristles attached to brush element 120. The oscillating motion of brush element 120 causes distribution of the pumped dentifrice material. Further distribution, as well as application of dentifrice material to the teeth result from the brushing and oscillating movement of both brush elements, 118 and 120.

Figures 6C, 6D, 6E:
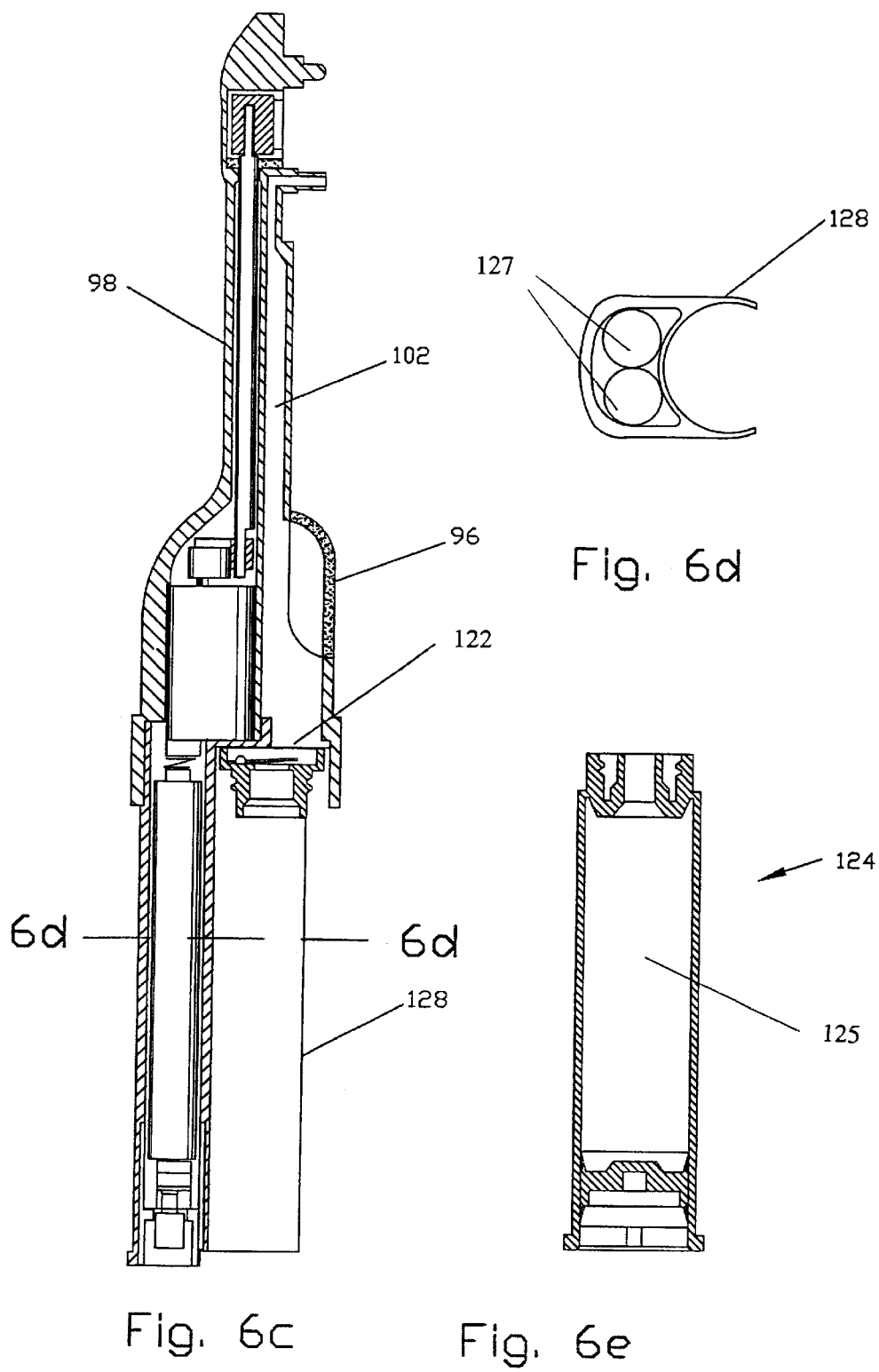
FIG. 6c is a cross section view of a dentifrice dispensing electrical toothbrush with a cartridge removed.
FIG. 6d is a cross section view showing the shape of the cartridge holding area.
FIG. 6e is a cross section view of a cartridge.

When all of the dentifrice material is depleted from cartridge 124, it is removed from the handle and replaced by a full cartridge. As shown in FIGS. 6c, 6d and 6e, cartridge 124 is placed in reservoir 125 of the brush handle which also contains a pair of batteries 127. Cartridge 124 is fastened by threads to one way check valve 122 and retained in position by holding arms 128 which are part of the outside wall of the handle. Holding arms 128 define the shape of the cartridge storage area so that it is compatible with the shape of the cartridge. This configuration facilitates cleaning and maintenance of the handle wall when the cartridge is replaced.

Figure 6F:
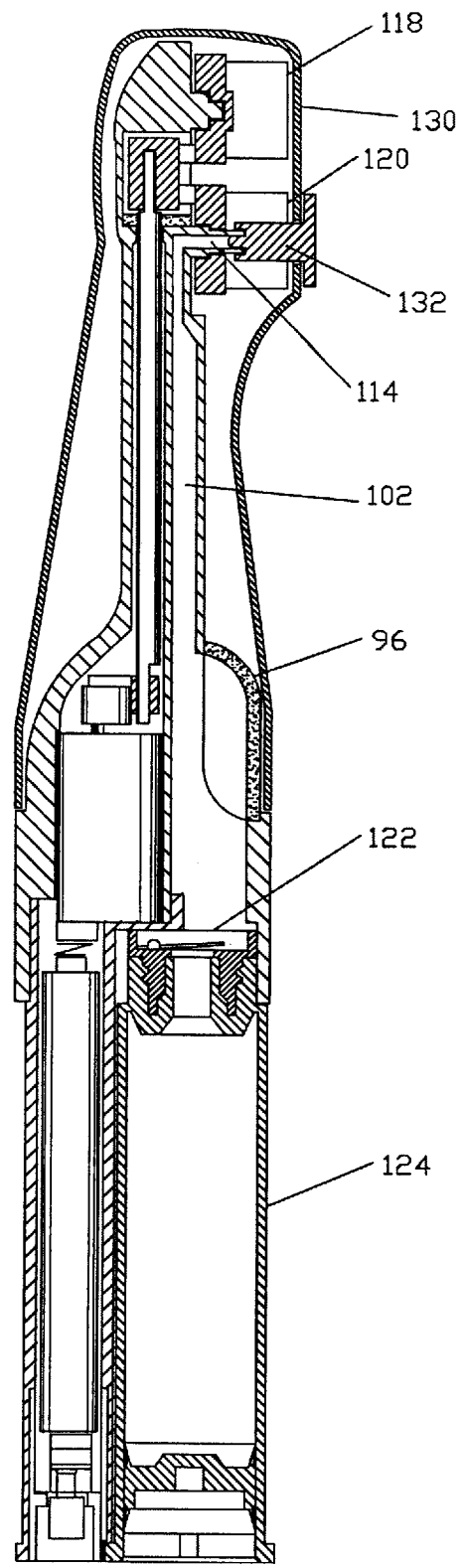
FIG. 6f is a cross section view of a dentifrice dispensing toothbrush with a cover and a plug attached.

Sealing of spout opening 114 of the dentifrice dispensing electrical toothbrush is similar to that described in U.S. Pat. No. 5,909,977 by Kuo. FIG. 6f shows sealing plug 132 being inserted into spout opening 114 to prevent the drying of dentifrice material. The positioning of the plug for sealing is facilitated by guides on cover 130 when the cover is at its fully closed and locked position on the shoulder of the brush handle.

Figures 4A, 4B:
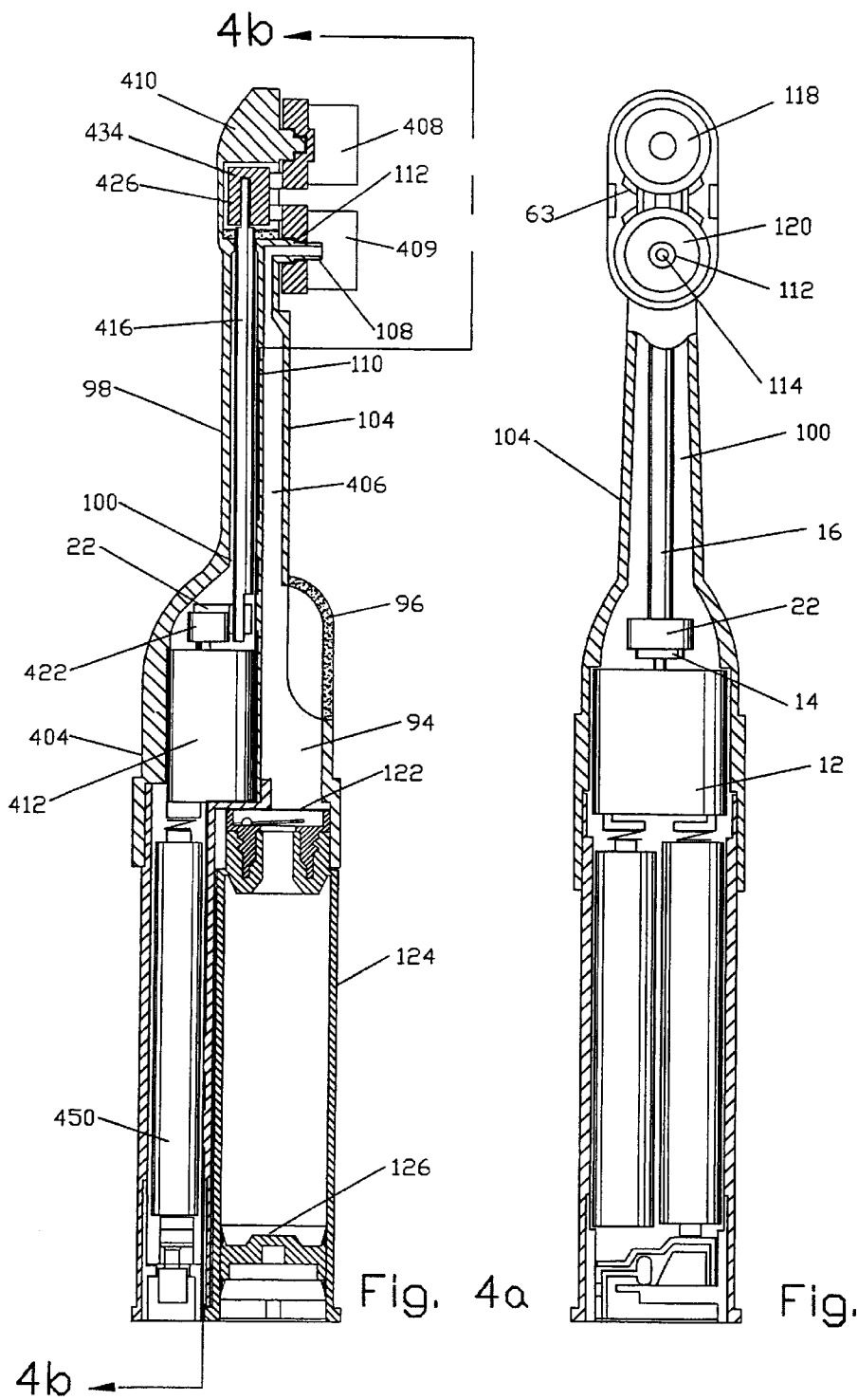
Figures 5A, 5B:
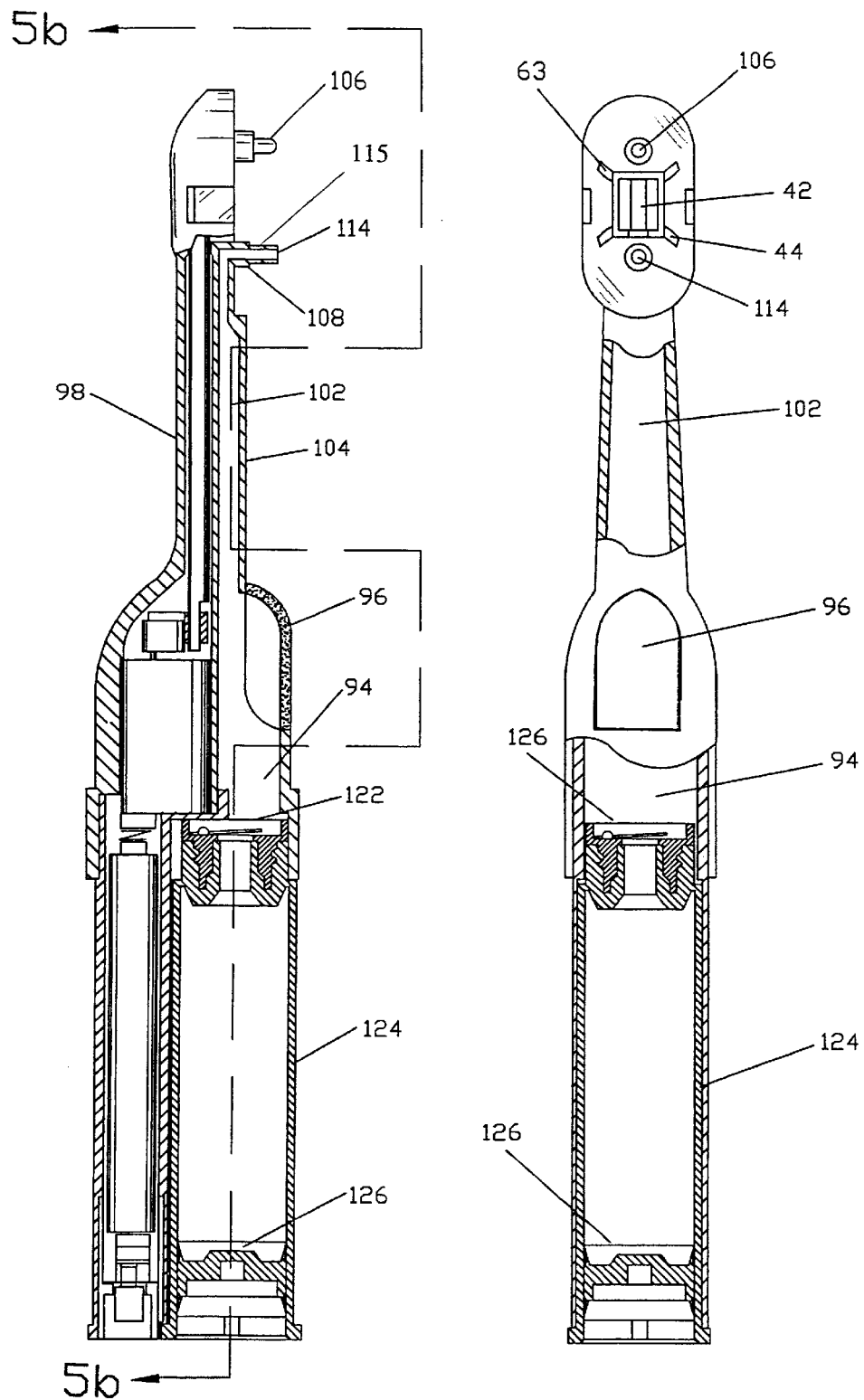
Figure 7:
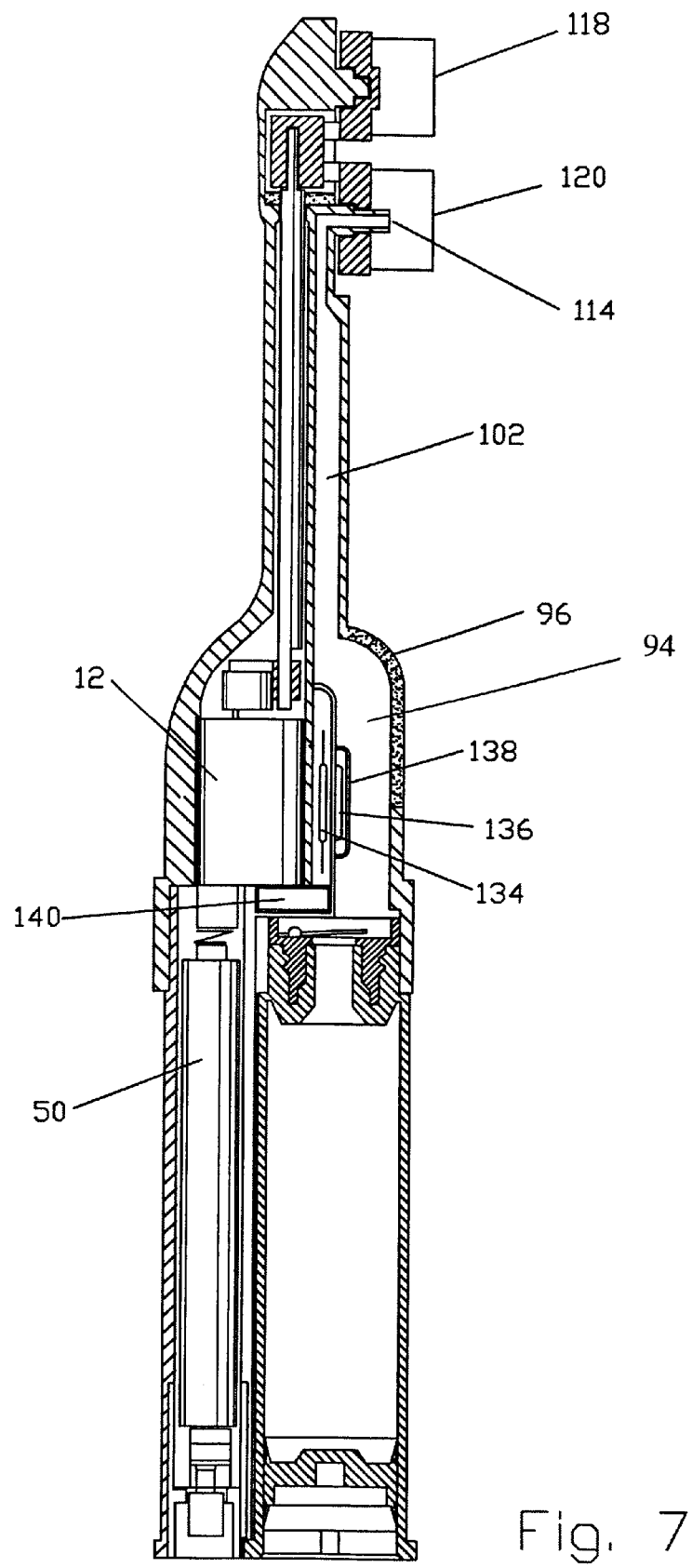
FIG. 7 is a cross section view of a dentifrice dispensing toothbrush with an internal switch and timer.

Two steps are required to ready the dentifrice dispensing electrical toothbrush shown in FIG. 4a for use. These include depressing an elastic compressible button to pump dentifrice material to the brush head and turning a switch to the "on" position to activate the motor for the drive mechanism. In accordance with the embodiment shown in FIG. 7, the steps of depressing the button and turning a switch to its "on" position for motor operation are combined into one step. This is particularly beneficial to the differently abled and to those with limited finger dexterity caused by maladies such as arthritis. The assembly for the one step system includes internal switch button 136 positioned inside of pump chamber 94. One side of button 136 is attached to membrane 138 so that it is isolated from the dentifrice material in the pump chamber. The remote side of the button is in juxtaposition to Reed switch 134 which is used to activate timer 140. When the pump chamber and all flow channels are filled with dentifrice material, compression of elastic compressible button 96 exerts hydrostatic pressure on membrane 138 because of the high resistance to the viscous flow of the dentifrice material through the channel and spout opening. Under the hydrostatic pressure, deflection of membrane 138 causes switch button 136 to activate Reed switch 134. Reed switch 134 has a permanent magnet which keeps motor 12 and timer 140 energized until a preset time period for the timer is expired. The circuits of the timer and the internal switch mechanism are designed to ignore further switching actions caused by repeated depressions of button 96 and concomitant pumping action on the dentifrice material for the duration of the preset time period of the timer. The dispensing action is usually accomplished within seconds since only a few repeated depressions of button 96 are required. In comparison, the motor is required to remain energized for the few minutes required for brushing.

In the manufacturing process, the spout, post, cap recess, two channeled neck, handle housing as well as the rubber button are co-injection molded as one integral piece. The rubber material for sealing the end of the channel of the neck is connected internally to the rubber button for simplifying the co-injection molding process. Also, in order to minimize seepage of cleaning water into the interface between the cartridge and the adjacent handle wall, a sealing rubber material is co-injection molded with the handle housing which causes a tight fit with the cartridge wall.

The invention has been described in detail with reference to preferred embodiments thereof. However, it is understood that variations and modifications can be effected within the spirit and scope of the invention.

I claim:
1. An electrical toothbrush comprising:
a. a handle;
b. a brush head having a platform with top and bottom surfaces and first and second posts which extend from the top surface;
c. a neck which connects the handle and the brush head;
d. a first replaceable brush element comprising a platform having a side wall between a top surface and a bottom surface, a circular recess in said bottom surface for detachably mounting the first replaceable brush element on the first post of said brush head, a notch in said side wall and a plurality of bristles attached to the top surface wherein the free ends of said bristles define a first brush surface;
e. a second replaceable brush element comprising a platform having a side wall between a top surface and a bottom surface, a circular recess in said bottom surface for detachably mounting the second replaceable brush element on the second post of said brush head, a notch in said side wall and a plurality of bristles attached to the top surface wherein the free ends of said bristles define a second brush surface;
f. a detachable retention cradle comprising a platform having a top surface, a bottom surface, and first and second openings through said platform surrounded by first and second retention rims for holding said first and second replaceable brush elements in a freely rotatable position on said first and second posts;
g. a motor positioned within said handle;
h. a drive shaft positioned within said neck and having a first end, a second end and a central longitudinal axis, said drive shaft being driveable by said motor; and
i. means for imparting an oscillating motion to the first and second replaceable brush elements through engagement with their side wall notches, said means being connected to the drive shaft.

2. The electrical toothbrush of claim 1 wherein the detachable retention cradle includes:
a. two opposing arms attached to the bottom surface of said platform, wherein each of said arms has corresponding opposing ribs for detachably engaging the brush head; and
b. two opposing tabs each having a base attached to the top surface of said platform and each having a remote end which terminates below said first and second brush surfaces, wherein inward deflection of the tabs toward each other causes outward deflection of the two opposing arms and their disengagement from the brush head.

3. The electrical toothbrush of claim 2 including deflectable ribbed catch arms attached to the bottom surface of said platform for retaining the first and second replaceable brush elements in said first and second retention rims when the retention cradle is disengaged from the brush head.

4. The electrical toothbrush of claim 2 including recess areas in the brush head for accommodating the opposing ribs of the two arms of said retention cradle.

5. The electrical toothbrush of claim 1 in which a tab extends radially outward from the first end of said drive shaft and is mateable with the notches in the side walls of said first and second replaceable brush elements.

6. The electrical toothbrush of claim 5 in which the means for imparting an oscillating motion to the first and second replaceable brush elements comprises a biased wheel connected to the motor and a profiled cam connected to the second end of said drive shaft.

7. The electrical toothbrush of claim 1 in which a cylindrical rod is attached to the first end of said drive shaft in a manner such that the central longitudinal axis of the cylindrical rod is parallel to and offset from the central longitudinal axis of the drive shaft, and wherein said cylindrical rod is mateable with the notches in the side walls of the platforms of said first and second replaceable brush elements.

8. The electrical toothbrush of claim 7 in which the means for imparting an oscillating motion to the first and second replaceable brush elements is comprised of the cylindrical rod mated with the notches in the side walls of the platforms of said elements.

9. The electrical toothbrush of claim 1 including:
   a. a first cylindrical rod attached to the first end of said drive shaft in a manner such that the central longitudinal axis of the first cylindrical rod is parallel to and offset from the central longitudinal axis of the drive shaft, said first cylindrical rod being mateable with the notch in the side wall of the platform of said second replaceable brush element; and
   b. a second cylindrical rod attached to the first cylindrical rod in a manner such that the central longitudinal axis of the second cylindrical rod is offset from the central longitudinal axis of the first cylindrical rod, said second cylindrical rod being mateable with the notch in the side wall of the platform of said first replaceable brush element.

10. The electrical toothbrush of claim 9 in which the means for imparting an oscillating motion to the first and second replaceable brush elements is comprised of the cylindrical rods engaged with the notches in the side walls of the platforms of said elements.

11. The electrical toothbrush of claim 9 wherein the second replaceable brush element is larger than the first replaceable brush element.

12. An electrical toothbrush comprising:
   a. a handle;
   b. a brush head having a platform with top and bottom surfaces and first and second posts which extend from the top surface;
   c. a neck which connects the handle and the brush head;
   d. a first replaceable brush element comprising a platform having a side wall between a top surface and a bottom surface, a circular recess in said bottom surface for detachably mounting the first replaceable brush element on the first post of said brush head, a notch in said side wall and a plurality of bristles attached to the top surface wherein the free ends of said bristles define a first brush surface;
   e. a second replaceable brush element comprising a platform having a side wall between a top surface and a bottom surface, a circular recess in said bottom surface for detachably mounting the second replaceable brush element on the second post of said brush head, a notch in said side wall and a plurality of bristles attached to the top surface wherein the free ends of said bristles define a second brush surface;
   f. a motor positioned within said handle;
   g. a drive shaft positioned within said neck and having a first end, a second end and a central longitudinal axis, said drive shaft being driveable by said motor; and
   h. means for imparting an oscillating motion to the first and second replaceable brush elements through engagement with their side wall notches, said means being connected to the drive shaft.

13. A dentifrice dispensing electrical toothbrush comprising:
   a. a handle having a reservoir for storing dentifrice material and pumping means for pumping dentifrice material from the reservoir;
   b. a brush head having:
      i. a platform with top and bottom surfaces;
      ii. an opening which extends through the platform;
      iii. a post which extends from the top surface of the platform;
      iv. a spout which extends from the top surface of the platform and is in communication with the opening in the platform;
   c. a neck which connects the handle and the brush head, said neck having an internal channel which is in communication with the reservoir and the opening in the brush head platform;
   d. a first replaceable brush element comprising a platform having a side wall between a top surface and a bottom surface, a circular recess in said bottom surface for detachably mounting the first replaceable brush element on the post of said brush head, a notch in said side wall and a plurality of bristles attached to the top surface wherein the free ends of said bristles define a first brush surface;
   e. a second replaceable brush element comprising a platform having a side wall between a top surface and a bottom surface, an opening in said bottom surface for detachably mounting the second replaceable brush element on the external wall of the spout opening which extends from the top surface of the brush head platform, a notch in said side wall and a plurality of bristles attached to the top surface wherein the free ends of said bristles define a second brush surface;
   f. a detachable retention cradle comprising a platform having a top surface, a bottom surface, and first and second openings through said platform surrounded by first and second retention rims for holding said first and second replaceable brush elements in a freely rotatable position on said first and second posts;
   g. a motor positioned within said handle;
   h. a drive shaft positioned within said neck and having a first end, a second end and a central longitudinal axis, said drive shaft being driveable by said motor; and
   i. means for imparting an oscillating motion to the first and second replaceable brush elements through engagement with their side wall notches, said means being connected to the drive shaft.

14. The dentifrice dispensing electrical toothbrush of claim 13 wherein the detachable retention cradle includes:
   a. two opposing arms attached to the bottom surface of said platform, wherein each of said arms has corresponding opposing ribs for detachably engaging the brush head; and
   b. two opposing tabs each having a base attached to the top surface of said platform and each having a remote end which terminates below said first and second brush surfaces, wherein inward deflection of the tabs toward each other causes outward deflection of the two opposing arms and their disengagement from the brush head.

15. The dentifrice dispensing electrical toothbrush of claim 14 including deflectable ribbed catch arms attached to the bottom surface of said platform for retaining the first and second replaceable brush elements in said first and second retention rims when the retention cradle is disengaged from the brush head.

16. The dentifrice dispensing electrical toothbrush of claim 14 including recess areas in the brush head for accommodating the opposing ribs of the two arms of said retention cradle.

17. The dentifrice dispensing electrical toothbrush of claim 13 in which a tab extends radially outward from the first end of said drive shaft and is mateable with the notches in the side walls of said first and second replaceable brush elements.

18. The dentifrice dispensing electrical toothbrush of claim 13 in which the means for imparting an oscillating motion to the first and second replaceable brush elements comprises a biased wheel connected to the motor and a profiled cam connected to the second end of said drive shaft.

19. The dentifrice dispensing electrical toothbrush of claim 13 in which a cylindrical rod is attached to the first end of said drive shaft in a manner such that the central longitudinal axis of the cylindrical rod is parallel to and offset from the central longitudinal axis of the drive shaft, and wherein said cylindrical rod is mateable with the notches in the side walls of the platforms of said first and second replaceable brush elements.

20. The dentifrice dispensing electrical toothbrush of claim 19 in which the means for imparting an oscillating motion to the first and second replaceable brush elements is comprised of the cylindrical rod mated with the notches in the side walls of the platforms of said elements.

21. The dentifrice dispensing electrical toothbrush of claim 13 including:
   a. a first cylindrical rod attached to the first end of said drive shaft in a manner such that the central longitudinal axis of the first cylindrical rod is parallel to and offset from the central longitudinal axis of the drive shaft, said first cylindrical rod being mateable with the notch in the side wall of the platform of said second replaceable brush element; and
   b. a second cylindrical rod attached to the first cylindrical rod in a manner such that the central longitudinal axis of the second cylindrical rod is offset from the central longitudinal axis of the first cylindrical rod, said second cylindrical rod being mateable with the notch in the side wall of the platform of said first replaceable brush element.

22. The dentifrice dispensing electrical toothbrush of claim 21 in which the means for imparting an oscillating motion to the first and second replaceable brush elements is comprised of the cylindrical rods engaged with the notches in the side walls of the platforms of said elements.

23. The dentifrice dispensing electrical toothbrush of claim 21 wherein the second replaceable brush element is larger than the first replaceable brush element.

24. A dentifrice dispensing electrical toothbrush comprising:
   a. a handle having a reservoir for storing dentifrice material and pumping means for pumping dentifrice material from the reservoir;
   b. a brush head having:
      i. a platform with top and bottom surfaces;
      ii. an opening which extends through the platform;
      iii. a post which extends from the top surface of the platform;
      iv. a spout which extends from the top surface of the platform and is in communication with the opening in the platform;
   c. a neck which connects the handle and the brush head, said neck having an internal channel which is in communication with the reservoir and the opening in the brush head platform;
   d. a first replaceable brush element comprising a platform having a side wall between a top surface and a bottom surface, a circular recess in said bottom surface for detachably mounting the first replaceable brush element on the post of said brush head, a notch in said side wall and a plurality of bristles attached to the top surface wherein the free ends of said bristles define a first brush surface;
   e. a second replaceable brush element comprising a platform having a side wall between a top surface and a bottom surface, an opening in said bottom surface for detachably mounting the second replaceable brush element on the external wall of the spout opening which extends from the top surface of the brush head platform, a notch in said side wall and a plurality of bristles attached to the top surface wherein the free ends of said bristles define a second brush surface;
   f. a motor positioned within said handle;
   g. a drive shaft positioned within said neck and having a first end, a second end and a central longitudinal axis, said drive shaft being driveable by said motor; and
   h. means for imparting an oscillating motion to the first and second replaceable brush elements through engagement with their side wall notches, said means being connected to the drive shaft.

25. The dentifrice dispensing electrical toothbrush of claim 24 including an elastic, compressible button for supplying a pumping force for the dentifrice material and for simultaneously activating a switch to energize the motor.

26. An electrical toothbrush comprising:
   a. a handle;
   b. a brush head having a platform with top and bottom surfaces and a post which extends from the top surface;
   c. a neck which connects the handle and the brush head;
   d. a replaceable brush element comprising a platform having a side wall between a top surface and a bottom surface, a circular recess in said bottom surface for detachably mounting the replaceable brush element on the post of said brush head, a notch in said side wall and a plurality of bristles attached to the top surface wherein the free ends of said bristles define a brush surface;
   e. a detachable retention cradle comprising a platform having a top surface, a bottom surface and an opening through said platform surrounded by a retention rim for holding said replaceable brush element in a freely rotatable position on said post;
   f. a motor positioned within said handle;
   g. a drive shaft positioned within said neck and having a first end, a second end and a central longitudinal axis, said drive shaft being driveable by said motor; and
   h. means for imparting an oscillating motion to the replaceable brush element through engagement with its side wall notch, said means being connected to the drive shaft.

27. A dentifrice dispensing electrical toothbrush comprising:
   a. a handle having a reservoir for storing dentifrice material and pumping means for pumping dentifrice material from the reservoir;
   b. a brush head having:
      i. a platform with top and bottom surfaces;

ii. an opening which extends through the platform;

iii. a post comprising a spout which extends from the top surface of the platform and is in communication with the opening in the platform;

c. a neck which connects the handle and the brush head, said neck having an internal channel which is in communication with the reservoir and the opening in the brush head platform;

d. a replaceable brush element comprising a platform having a side wall between a top surface and a bottom surface, an opening in said bottom surface for detachably mounting the replaceable brush element on the external wall of the spout opening which extends from the top surface of the brush head platform, a notch in said side wall and a plurality of bristles attached to the top surface wherein the free ends of said bristles define a brush surface;

e. a detachable retention cradle comprising a platform having a top surface, a bottom surface and an opening through said platform surrounded by a retention rim for holding said replaceable brush element in a freely rotatable position on said post;

f. a motor positioned within said handle;

g. a drive shaft positioned within said neck and having a first end, a second end and a central longitudinal axis, said drive shaft being driveable by said motor; and h. means for imparting an oscillating motion to the replaceable brush element through engagement with its side wall notch, said means being connected to the drive shaft.

* * * * *